(12) United States Patent  
Weibel et al.

(10) Patent No.: US 9,289,123 B2  
(45) Date of Patent: Mar. 22, 2016

(54) CONTACT LENS FOR MEASURING INTRAOCULAR PRESSURE

(71) Applicant: Verily Life Sciences LLC, Mountain View, CA (US)

(72) Inventors: Douglas Weibel, Madison, WI (US); Babak Parviz, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 52 days.

(21) Appl. No.: 14/107,862

(22) Filed: Dec. 16, 2013

(65) Prior Publication Data

US 2015/0164321 A1  Jun. 18, 2015

(51) Int. Cl.
- *A61B 5/00* (2006.01)
- *A61B 3/16* (2006.01)
- *A61B 3/18* (2006.01)

(52) U.S. Cl.
CPC .... *A61B 3/16* (2013.01); *A61B 3/18* (2013.01)

(58) Field of Classification Search
CPC .............. A61B 3/00; A61B 3/10; A61B 3/16; A61B 3/18

See application file for complete search history.

(56) References Cited

U.S. PATENT DOCUMENTS

| | | |
|---|---|---|
| 4,628,938 A | 12/1986 | Lee |
| 2003/0014021 A1 | 1/2003 | Holmen |
| 2007/0129623 A1 | 6/2007 | Fleischman et al. |
| 2009/0076367 A1 | 3/2009 | Sit et al. |
| 2010/0234717 A1 | 9/2010 | Wismer |
| 2011/0040161 A1 | 2/2011 | Abreu |
| 2012/0238857 A1 | 9/2012 | Wong |
| 2012/0289810 A1 | 11/2012 | Ehrecke |
| 2013/0041245 A1 | 2/2013 | Cerboni |
| 2013/0130232 A1 | 5/2013 | Weibel et al. |
| 2013/0184554 A1 | 7/2013 | Elsheikh et al. |
| 2013/0225968 A1 | 8/2013 | Auvray |

FOREIGN PATENT DOCUMENTS

EP  1401327 B1  8/2006

OTHER PUBLICATIONS

Search Report and Written Opinion for PCT/US2014/070569 mailed Apr. 17, 2015.

*Primary Examiner* — Max Hindenburg  
(74) *Attorney, Agent, or Firm* — McDonnell Boehnen Hulbert & Berghoff LLP

(57) ABSTRACT

An eye-mountable device for measuring an intraocular pressure is provided. The device may include a transparent polymeric material having a concave surface configured to be removably mounted over a corneal surface of an eye, an antenna, an expandable member, a sensor and control electronics at least partially embedded in the transparent polymeric material. The expandable device is configured to expand and apply a force to the corneal surface and the sensor is configured to detect a resistance to deformation of the cornea in response to the applied force. The resistance to deformation of the cornea in response to the force applied by the expandable member is indicative of the intraocular pressure of the eye.

16 Claims, 9 Drawing Sheets

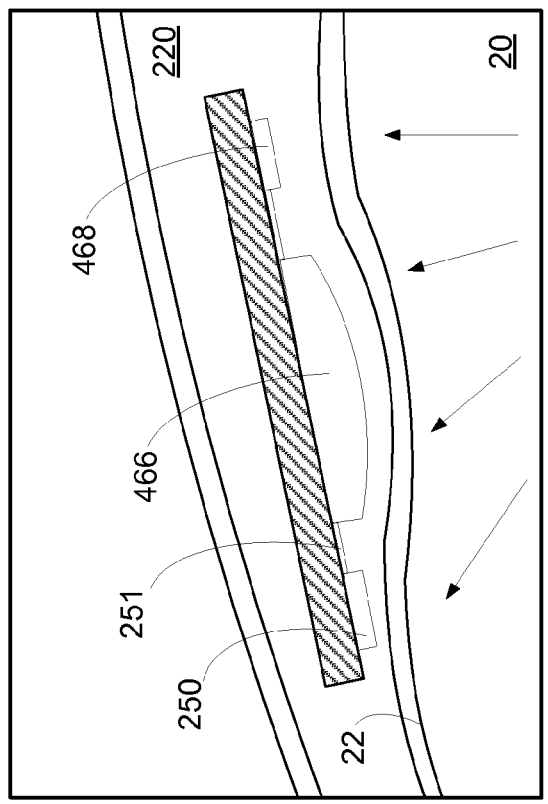
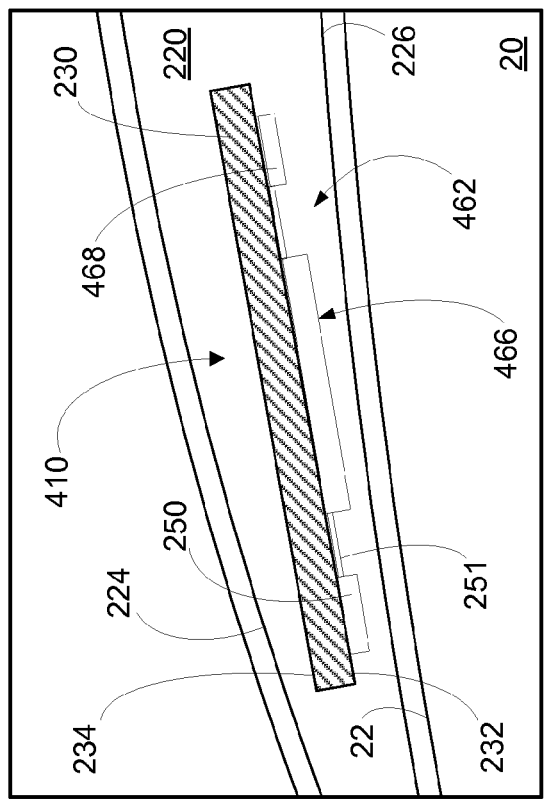
FIG. 4A
FIG. 4B

CONTACT LENS FOR MEASURING INTRAOCULAR PRESSURE

BACKGROUND

Unless otherwise indicated herein, the materials described in this section are not prior art to the claims in this application and are not admitted to be prior art by inclusion in this section.

Ocular hypertension and glaucoma are conditions of the eye characterized by, or resulting from, increased intraocular pressure (IOP). Those afflicted with ocular hypertension exhibit higher than normal IOP in the absence of optic nerve damage or visual field loss, while glaucoma describes a group of ocular disorders displaying characteristic IOP-associated optic neuropathy. Elevated IOP is the most important risk factor for glaucoma, so those with ocular hypertension are frequently considered to have a greater chance of developing the condition. Over time, increased IOP can lead to permanent damage of the optic nerve and resultant visual field loss, which, if left untreated, can progress to blindness.

Intraocular pressure is primarily dictated by the liquid aqueous humor, which is produced by the ciliary body of the eye. Changes in the balance between the production of the aqueous humor and the drainage of the fluid through the trabecular meshwork in the eye can increase the pressure within the eye (i.e., IOP). Routine measurement of IOP can be used to diagnose hypertension and glaucoma, which guide treatment regimens using a range of drugs (for example, the aryl- and alkyl-sulfonamides, which inhibit carbonic anhydrase and decrease intraocular pressure). Normal IOP is typically between 10 mmHg and 21 mmHg.

Intraocular pressure is typically measured during comprehensive eye examinations using various techniques, most notably tonometry. These measurements are typically conducted by ophthalmologists, optometrists, clinicians or other trained professionals using a tonometer in clinical offices. A variety of different tonometers have been developed. Some devices are hand-held, but many are large enough to restrict their portability (for example, the rebound tonometer). Because operation of these devices requires technical training, a visit to a physician's office is required, which can be inconvenient for the patient. Moreover, there are several situations where access to ophthalmologists or traditional tonometry devices are very limited or even unavailable, such as, in developing countries and rural or other limited health care environments, in emergency rooms, or in remote clinical sites. Current tonometry tests are also fairly invasive, involving direct contact with the eye to take a pressure measurement, or puffed air, which often causes the patient to flinch or blink. In some cases, multiple attempts must be made to obtain readings, which can be very difficult for children and infants, who can be restless and uncooperative. Further, fitness, exercise, nutrition (e.g. caffeine, alcohol, and glycerol), the time of day, and other variables can influence intraocular pressure, which poses challenges to one-point measurements that must be made in a physician's or optometrist's office.

SUMMARY

Some embodiments of the present disclosure provide a body-mountable device including: (1) a transparent polymeric material having a concave surface and a convex surface, wherein the concave surface is configured to be removably mounted over a corneal surface of an eye and the convex surface is configured to be compatible with eyelid motion when the concave surface is so mounted; (2) an antenna at least partially embedded in the transparent polymeric material; (3) an expandable member at least partially embedded in the transparent polymeric material and configured to expand and apply a force to the corneal surface; (4) a sensor at least partially embedded in the transparent polymeric material configured to detect a resistance to deformation of the cornea in response to the force applied by the expandable member; and (5) control electronics at least partially embedded in the transparent polymeric material, wherein the control electronics are configured to: (i) use the sensor to measure the resistance to deformation of the cornea; and (ii) use the antenna to communicate data indicative of the measured resistance to deformation of the cornea to an external reader, wherein the resistance to deformation of the cornea in response to the force applied by the expandable member is indicative of intraocular pressure of the eye.

Further embodiments of the present disclosure provide a method including: (1) applying, by expansion of an expandable member in an eye-mountable device, a force to a corneal surface; (2) measuring, by a sensor in the eye-mountable device, a resistance to deformation of the cornea in response to the force applied by the expandable member; and (3) communicating, by an antenna in the eye-mountable device, data indicative of the measured resistance to deformation of the cornea.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 4A-4B are side cross-section views enhanced to show the example eye-mountable device when mounted against the cornea of an eye and operation of an intraocular pressure sensor including an expandable member, in accordance with an example embodiment.

DETAILED DESCRIPTION

Figure 1:
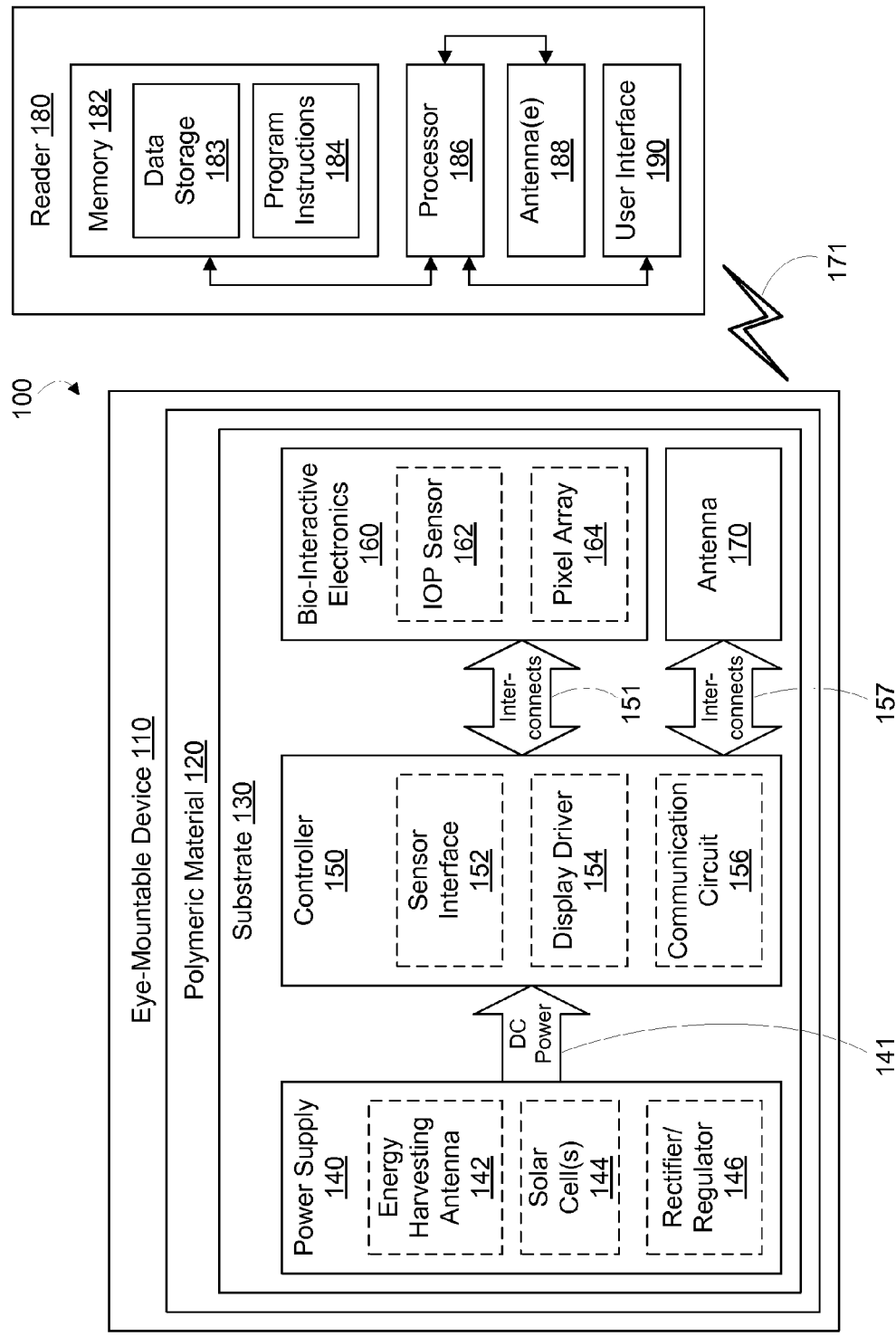
FIG. 1 is a block diagram of an example system that includes an eye-mountable device in wireless communication with a reader, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

A contact lens can have an embedded sensor for measuring IOP. In some examples, the sensor may be provided as a strain gauge embedded in the contact lens having electrical components for actuation of or sensing the displacement of the gauge and transmitting data back to the user through a remote interface. The gauge may be provided in a range of geometries, configurations and materials. The sensor elements may be arranged out of the field of view of the contact lens, such as around the lens center, so as to not interfere with the wearer's vision.

In a first aspect, the IOP sensor may comprise an expandable member configured to apply a force to the surface of the eye and one or more sensors for measuring a change in configuration of the expandable member, such as deflection, deformation or displacement, due to the application of force against the eye. Generally, the higher the IOP, the more resistant the eye will be to deformation by an expandable member pressing against it. Accordingly, the higher the IOP, the greater the deflection, deformation or displacement of the sensor will be. The deflection, deformation or displacement of the sensor may be measured optically, by a change in resistance, capacitance or conductance in one or more co-planar strain gauges, or by a change in capacitance or conductance in one or more pairs of electrodes placed in parallel planes on the expandable member.

For example, the expandable element may comprise a layer of material that is rapidly converted from a solid to a gas. Generally, any material which produces $CO_2$, $O_2$ or $N_2$ gas may be used, such as sodium, potassium, or lithium azide. In one example, dried sodium azide (a propellant used in automobile airbags) may be deposited in a channel fabricated into the contact lens in electrical contact with a pair of wires or electrodes. An applied electrical signal causes the decomposition of sodium azide to release nitrogen gas, which forms at a rate much faster than the diffusion of the gas in the silicone polymer, thereby causing a ballooning effect of the sensor that presses it against the cornea. The resistance to the expanding device can be measured using a range of different modalities. In operation, approximately 50 micrograms of sodium azide may be sufficient to create approximately 50 microliters of nitrogen gas in less than a tenth of a second. Multiple chambers may be disposed around the contact lens to take additional IOP measurements over time.

In a second example, the expandable member may be provided as a layer of an electroactive or conducting polymer with defined stiffness that expands when an electrical current is applied to it through an attached electrode. The electroactive polymer may be polypyrrole, polythiophene, polyaniline, and polyacetylene. Expansion of the polymer layer causes the material to push against the cornea and the deflection or displacement of the polymer layer by the cornea may be detected optically or may be measured by a second electrode (or pair of electrodes). Alternatively, the deformation of the polymer against the cornea may be quantified using a strain gauge. A feedback circuit may also be provided to determine the amount of current required to obtain a measured level of expansion of the polymer layer. A layer of hydrogel may also be used as an expandable member.

In a third example, the expandable member may be provided as a chamber or channel in the contact lens which expands by the degas-driven flow of liquid into the chamber or channel. The de-gassed contact lens may be stored under vacuum. As the degassed lens equilibrates to atmospheric pressure, the pressure differential between the polymer and the atmosphere creates a self-pumping mechanism. Fluid fills the chamber and displaces gas, which may escape through the silicone lens, which is relatively transparent to gas. The inflow of fluid or liquid causes the expansion of the chamber which pushes against the cornea. The amount of fluid or liquid pumped into the chamber will depend on the chamber's ability to expand against the cornea, which will depend on the deformability of the cornea and, therefore, the IOP. Accordingly, the IOP may be determined by the rate of pumping or total volume of fluid pumped into chamber. Deflection of the chamber against the corner may be measured optically or electrically.

Additionally or alternatively, the IOP sensor may be provided as a strain element or an array of strain elements disposed on or embedded in the contact lens material which detects IOP through some direct deformation or deflection of the sensor due to a change in curvature and/or circumference of the surface of the eye. For example, the sensor may include a resistive strain element or an array of co-planar resistive strain elements, such as ring electrodes. The strain element(s) may be made, at least partly, of a resistive or piezoresistive material, the resistance of which varies based on the gauge strain or deformation. In operation, a change in IOP causing a change the circumference of the eye will, in turn, result in a change in the circumference of a contact lens situated on the eye. The resulting deformation of the strain element(s) on the contact lens changes the resistance of the material, thereby changing the current flowing through the element(s). Voltage may be measured across the terminals of the strain element(s) to determine a change in resistance of the strain element(s). The measured change in resistance of the strain gauge may be equated to the change in IOP of the wearer of the device. In some examples, the strain elements(s) may be configured as a Wheatstone bridge.

The strain element may also be provided as a capacitive sensor comprising an array of electrically connected electrodes lying in parallel planes within the contact lens. A change in IOP will change the curvature of the surface of the eye and, as a result, the curvature of the contact lens and the distance between the electrodes of the sensor. The change in distance between the electrodes will change the electric field between them, thereby changing the capacitance of the sensor. The measured change in capacitance across the sensor may be equated to the change in IOP.

In another aspect, the sensor may be provided as a set of or an array of co-planar interdigitated electrodes. Deflection of the contact lens by a change in IOP will change the distance between the fingers of the electrodes, causing a measurable change in conductance or capacitance of the sensor from which IOP may be determined.

The above-described contact-lens based technology may allow individuals to make continuous or more frequent tonometry measurements at home using a less invasive and more convenient method than the tonometry devices available in physician's offices. IOP measurements taken by the contact-lens platform may also be used to control an on-lens drug delivery mechanism. This technology may also be applied to animals: both small animal care (large financial market for animal care) and large animal/livestock care (again a large market).

Upon taking the measurements, the IOP sensor may store data related to the measurements, and subsequently send the data upon request from a remote interface, such as a reader. The reader, in turn, can store and/or process the received data. For example, the sensor can take resistance measurements and send data about the measured resistance(s) to the reader. The reader can process the resistance measurement data to determine IOP-related information about the wearer. The reader may communicate with the sensor electronics and thereby obtain IOP data from the contact lens according to one or more standards, such as, but not limited to, a RFID standard, a Bluetooth standard, a Wi-Fi standard, a Zigbee standard, etc. Further, the reader can communicate the raw or processed data using a Bluetooth or other communication protocol interface to another device, such as a display device or the cloud.

It should be understood that the above embodiments, and other embodiments described herein, are provided for explanatory purposes, and are not intended to be limiting.

II. Example Ophthalmic Electronics Platform

FIG. 1 is a block diagram of a system 100 that includes an eye-mountable device 110 in wireless communication with a reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an intraocular pressure (IOP) sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate IOP sensor 162. As will be discussed further below, the IOP sensor 162 can include, for example, an expandable member for applying a force to the corneal surface and a deformation sensor for detecting the cornea's resistance to the force applied by the expandable member. In some aspects, the deformation sensor may measure the cornea's resistance to deformation by any mechanical, optical, acoustical, pneumatic, and electrical means. Alternatively, the IOP sensor 162 can be, for example, a strain gauge configured to detect a strain on the transparent polymeric material in response to a change in curvature of the corneal surface indicative of a change in intraocular pressure. A voltage can be applied across the strain gauge or deformation sensor and a change in an electrical property (i.e. residence, capacitance, inductance, etc.) can be measured. The change in the electrical property is proportional to the strain experienced by the sensor, which can be due to the force applied to the corneal surface by the expandable member, or a passive change in curvature of the corneal surface. Thus, the measured change in the electrical property can provide an indication of intraocular pressure.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can be configured to be external to the eye; i.e., is not part of the eye-mountable device. Reader 180 can include one or more antennae 188 to send and receive wireless signals 171 to and from the eye-mountable device 110. In some embodiments, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Example processor(s) include, but are not limited to, CPUs, Graphics Processing Units (GPUs), digital signal processors (DSPs), application specific integrated circuits (ASICs). Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the IOP sensor 162), program settings (e.g., to adjust behavior of the eye-mountable device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the eye-mountable device 110 (e.g., sensor outputs from the IOP sensor 162). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

A user interface 190 may also be provided on reader 180. User interface 190 can include an indicator, such as but not limited to one or more light-emitting diodes (LEDs), that can indicate that reader 180 is operating and provide some information about its status. For example, reader 180 can be configured with an LED that displays one color (e.g., green) when operating normally and another color (e.g., red) when operating abnormally. In other embodiments, the LED(s) can change display when processing and/or communicating data in comparison to when idle (e.g., periodically turn on and off while processing data, constantly stay on or constantly stay off while idle).

In some embodiments, one or more of the LED(s) of user interface 190 can indicate a status of sensor data; e.g., not display when sensor data are either within normal range(s) or unavailable, display in a first color when sensor data are either outside normal range(s) but not extremely high or low, and display a second color when the sensor data are extremely high and/or low. For example, if sensor data indicate that intraocular pressure levels are extremely high or low, user interface 190 can be instructed by processor 186 to display using the second color. In particular embodiments, user interface 190 can include a speaker or other sound-emitting device to permit reader 180 to generate sounds; e.g., warning sound(s) and/or tone(s) if sensor data are extremely high and/or low. Reader 180 can also have one or more buttons and/or other devices to receive inputs. For example, reader 180 can have a button for a user to indicate when an eye-mountable device has been placed on his or her eye.

In some embodiments, reader 180 can be a smart phone, digital assistant, or other portable computing device with wireless connectivity sufficient to provide the wireless communication link 171. In other embodiments, reader 180 can be implemented as an antenna module that can be plugged in to a portable computing device; e.g., in scenarios where the communication link 171 operates at carrier frequencies not commonly employed in portable computing devices. In other examples, the reader may be provided as a wearable computing device, which may be any device capable of being mounted or worn at, on, in or in proximity to a body. For example, the reader 180 can be integrated in a pair of eyeglasses, a piece of jewelry such as a necklace, earring, wristwatch, etc. or integrated in an article of clothing worn near the head, such as a hat, headband, etc.

In an example where the eye-mountable device 110 includes an IOP sensor 162, the system 100 can be operated to monitor the intraocular pressure of the eye. Thus, the eye-mountable device 110 can be configured as a platform for an ophthalmic IOP sensor. The level of intraocular pressure can affect a number of measurable properties of the eye, including both the shape and stiffness of the eye. For example, typically, the higher the intraocular pressure, the more resistant the cornea will be to deformation. Accordingly, intraocular pressure may be measured by measuring resistance of the eye to deformation by an applied force. In other aspects, because the envelope of the eye is flexible and because intraocular pressure is related to the volume of aqueous humor within the eye, as intraocular pressure changes, the curvature and/or circumference of the surface of the eye may also change. Accordingly, intraocular pressure may be measured by measuring a physical change at the surface of the eye. Measuring resistance to deformation or change in shape of the eye with an eye-mountable device provides a convenient and non-invasive technique for monitoring intraocular pressure in comparison to tonometry techniques performed with typical tonometers. Moreover, the ophthalmic IOP sensor platform disclosed here can be operated substantially continuously to enable real-time or more frequent monitoring of intraocular pressure.

To perform a reading with the system 100 configured as an intraocular pressure monitor, the reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the IOP sensor 162 to measure intraocular pressure. For example, the sensor interface module 152 can cause an expandable member in the IOP sensor 162 to expand and apply a force to the corneal surface. The sensor interface module 152 can further apply a voltage across a strain gauge or deformation sensor in the IOP sensor 162 to detect the cornea's resistance to deformation by the expandable member. The applied voltage can be sufficient to detect a change in electrical property of the strain gauge. The measured change in electrical property, such as resistance, can provide the sensor reading ("result") indicative of the intraocular pressure.

The controller 150 can operate the antenna 170 to communicate the sensor reading back to the reader 180 (e.g., via the communication circuit 156). The sensor reading can be communicated by, for example, modulating an impedance of the communication antenna 170 in accordance with the detected change in electrical property of the strain gauge or deformation sensor, such that the modulation in impedance is detected by the reader 180. The modulation in antenna impedance can be detected by, for example, backscatter radiation from the antenna 170.

The reader 180 can associate the backscatter signal with the sensor result (e.g., via the processor 186 according to a pre-programmed relationship associating impedance of the antenna 170 with output from the IOP sensor 120). The processor 186 can then store the indicated sensor results (e.g., intraocular pressure values) in a local memory and/or an external memory (e.g., by communicating with the external memory either on a remote device or through a network). In some embodiments, reader 180 can communicate with devices in addition to eye-mountable device 110, such as a display device, a remote computing device, or a remote server.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the reader 180 can accumulate a set of analyte concentration measurements over time without continuously powering the eye-mountable device 110.

Figure 2A:
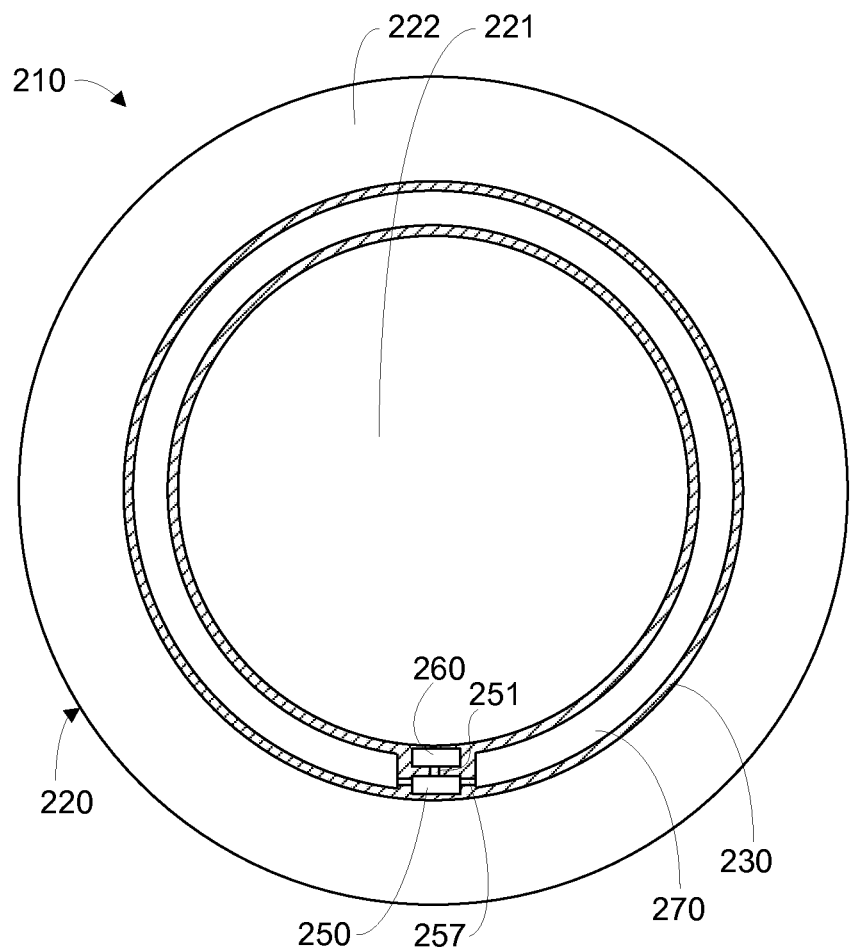
FIG. 2A is a bottom view of an example eye-mountable device, in accordance with an example embodiment.
Figure 2B:
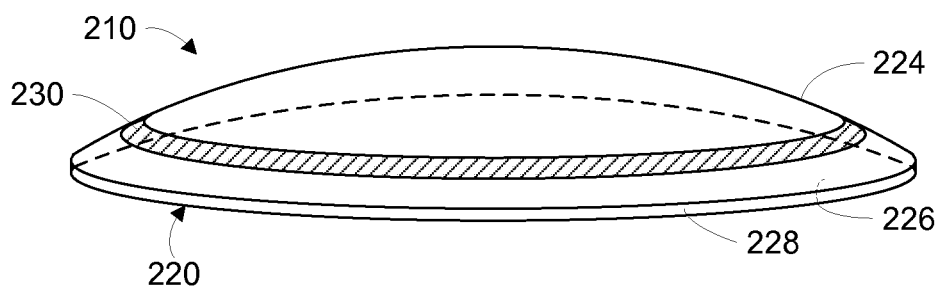
FIG. 2B is a side view of the example eye-mountable device shown in FIG. 2A, in accordance with an example embodiment.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. In some embodiments, eye-mountable device 210 can include some or all of the above-mentioned aspects of eye-mountable device 110. In other embodiments, eye-mountable device 110 can further include some or all of the herein-mentioned aspects of eye-mountable device 210.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an IOP sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the eye-mountable device 210, bio-interactive electronics 260 is mounted to a side of the substrate 230 facing the convex surface 224. Where the bio-interactive electronics 260 includes an IOP sensor, for example, mounting such a bio-sensor on the substrate 230 facing the convex surface 224 allows the bio-sensor to detect a resistance to deformation or change in confirmation of the corneal surface. In some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the loop antenna can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
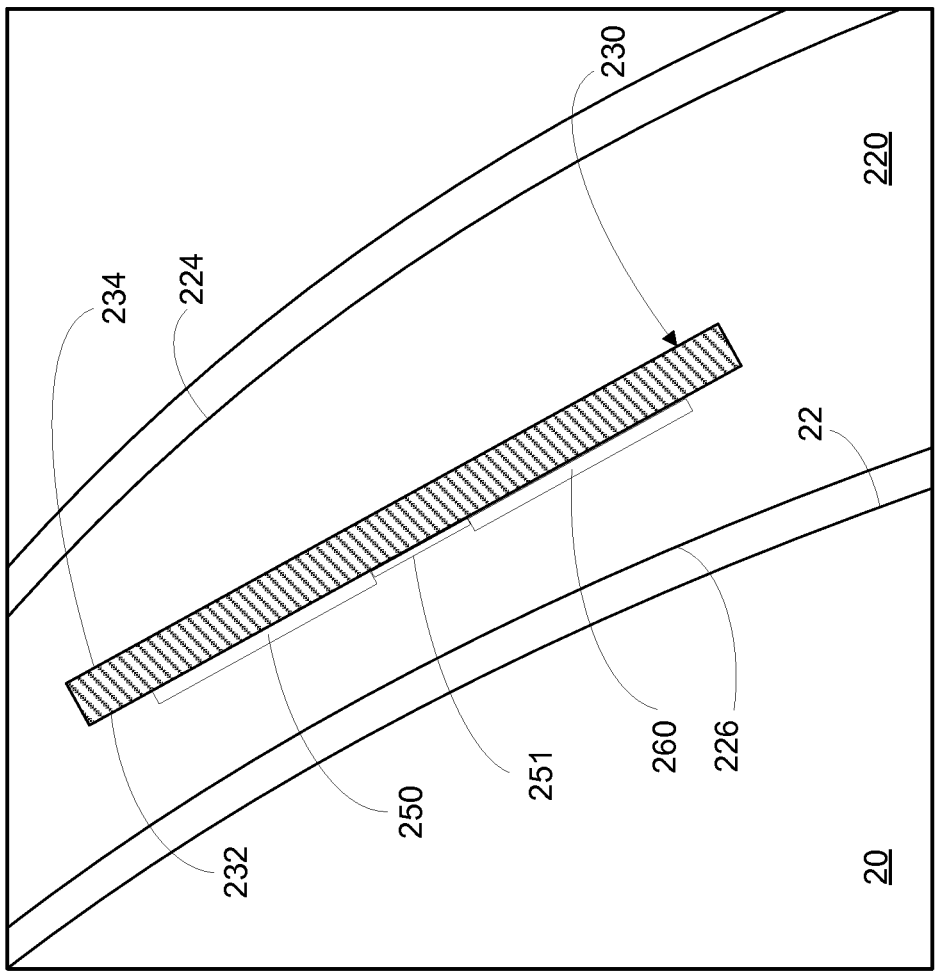
FIG. 2D is a side cross-section view enhanced to show the tear film layers surrounding the surfaces of the example eye-mountable device when mounted as shown in FIG. 2C, in accordance with an example embodiment.
Figure 2C:
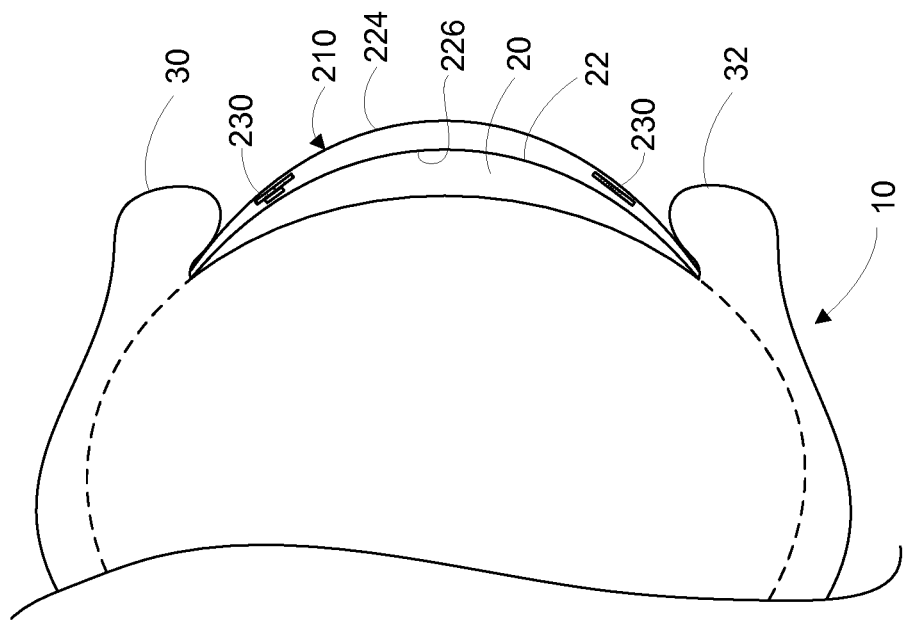
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the example eye-mountable device 210 adjacent to the cornea 20. It is noted that relative dimensions in FIGS. 2C and 2D are not necessarily to scale, but have been rendered for purposes of explanation only in describing the arrangement of the example eye-mountable electronic device 210. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. A layer of tear film disposed on the corneal surface 22 may facilitate mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the inward-facing surface 232 such that the bio-interactive electronics 260 are facing concave surface 226.

The polymer layer defining the posterior side may be greater than 50 micrometers thick, whereas the polymer layer defining the anterior side may be less than 150 micrometers. Thus, bio-interactive electronics 260 may be at least 50 micrometers away from the convex surface 224 and may be a greater distance away from the concave surface 226. The bio-interactive electronics 260 could also be positioned closer to the concave surface 226 than the convex surface 224.

III. Example Intraocular Pressure Sensor

FIGS. 3A-3B, 4A-4B, 5A-5B and 6A-6B are side cross-sectional views illustrating various example intraocular pressure sensors for use in an eye-mountable device as described above with respect to FIGS. 1 and 2A-2D. These Figures are close-in views enhanced to show the example eye-mountable devices adjacent to the cornea 20.

Figure 3B:
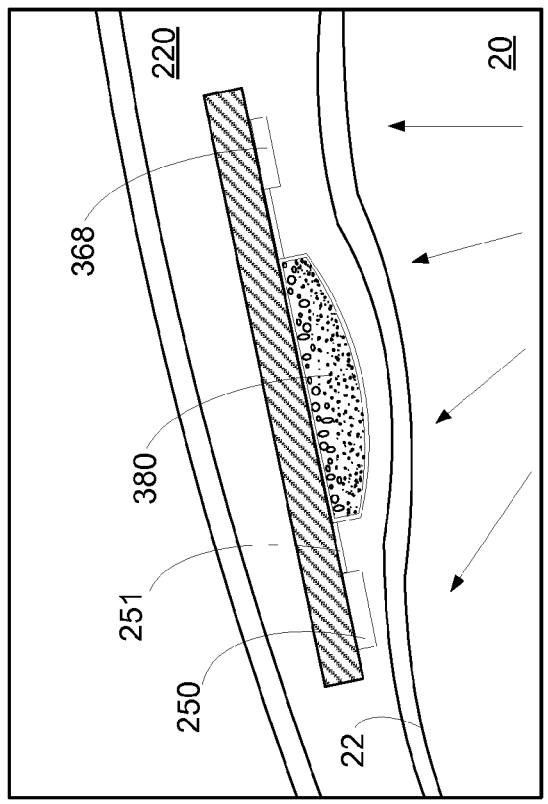
FIGS. 3A-3B are side cross-section views enhanced to show the example eye-mountable device when mounted against the cornea of an eye and operation of an intraocular pressure sensor including an expandable member, in accordance with an example embodiment.
Figure 3A:
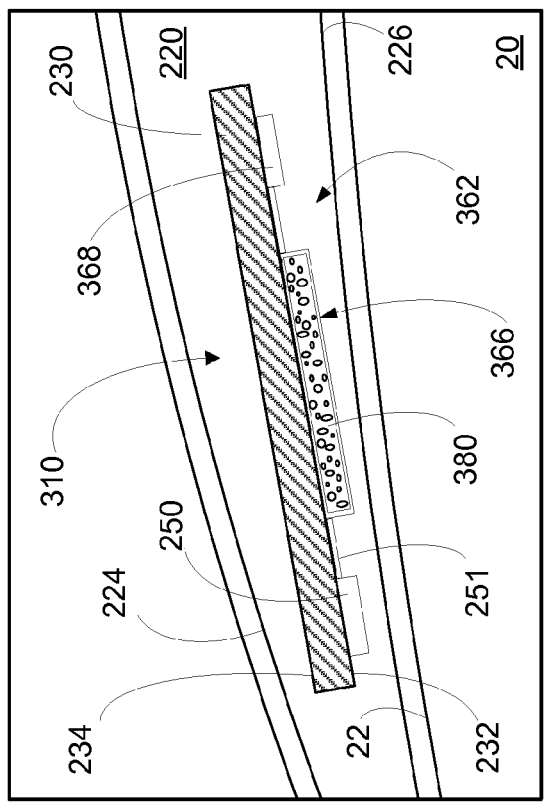

FIGS. 3A-3B illustrate a portion of an eye-mountable device 310 in contact with the surface 22 of a cornea 20 of an eye. Similar to that described above, the substrate 230 may be provided as a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. Controller 250, conductive interconnect 251 and bio-interactive electronics, including an intraocular pressure sensor 362, are mounted on the inward-facing surface 232 of the substrate 230. Intraocular pressure sensor 362 includes an expandable member 366 for applying a force to the corneal surface 22 and a deformation sensor 368 for measuring the cornea's 20 resistance to that force. Intraocular pressure may be derived from the cornea's resistance to deformation.

In this example, expandable member 366 may be provided as a layer of material configured to undergo a phase change, resulting in expansion of the material. For example, the material may rapidly convert from a solid to a gas. Any material which produces $CO_2$, $O_2$ or $N_2$ gas may be used, such as sodium, potassium, or lithium azide. In one aspect, dried sodium azide (a propellant used in automobile airbags) may be deposited in a channel 380 in electrical contact with a pair of wires or electrodes, such as interconnect 251. Channel 380, which may be provided in any number of shapes (such as a circumferential ring or an array of individual channels) may be fabricated directly in the polymeric material 220 or disposed on the substrate 230. When an electrical signal is applied to the channel 380 via interconnect 251, the sodium azide is caused to decompose and release nitrogen gas. Because the nitrogen gas forms within the channel 380 at a rate much faster than the diffusion of the gas in the silicone polymer material 220, the expandable member 366 expands and presses against (or causes a layer of polymeric material 220 to press against) the cornea 20. Approximately 50 micrograms of sodium azide may be sufficient to create approximately 50 microliters of nitrogen gas in less than a tenth of a second.

The eye-mountable device 310 may be designed to take a single IOP measurement, or multiple IOP measurements over time. Because the decomposition of solid sodium azide is not reversible, once the sodium azide in a channel 380 has converted to nitrogen gas (and other byproducts), that channel 380 is not used again as part of the expandable member to apply a force to the corneal surface (unless, for example, it is recharged with more material off-eye). Accordingly, if the expandable member 366 of the eye-mountable device 310 has a single channel 380, then the eye-mountable device 310 may be removed from the eye and discarded after an IOP measurement has been taken. In some examples, the user may be under an intra-ocular pressure monitoring regimen by a clinician, ophthalmologist or physician and may have instructions to subsequently insert another eye-mountable device 310 for taking another IOP measurement at a later time. For example, a monitoring regimen may include taking an IOP measurement once every two hours, removing the spent eye-mountable device 310 and promptly inserting a new eye-mountable device 310. In other examples, the expandable member 366 of the eye-mountable device 310 may include an array of multiple sodium azide-filled cannels 380. The eye-mountable device 310 may be configured to apply an electrical signal to individual channels 380 of the array over time so as to take multiple IOP measurements. Once all of the channels 380 in the array are spent, the user may be instructed to remove the eye-mountable device 310.

FIGS. 4A-4B illustrate another example eye-mountable device 410. In this example, the IOP sensor 462 includes an expandable member 466 and a deformation sensor 468. The expandable member 466 may be provided as a layer of an electroactive or conducting polymer with defined stiffness that expands when an electrical current is applied to it, such as through interconnect 251. The electroactive polymer may be any polymer that exhibits a change in size or shape when stimulated by an electric field, such as polypyrrole, polythiophene, polyaniline, and polyacetylene, and may be mounted or deposited directly on the substrate 230. In some examples, a hydrogel may also be used as an expandable member. The expandable member 466 may be provided in the form of a circumferential ring of electroactive polymer, or may be provided as an array of individual electrically-connected deposits of the electroactive polymer. The controller 250 may be configured to control when an electric current is applied to the expandable member 466 via interconnect 251 and, thereby, control expansion of the expandable member 466. As shown in FIG. 4B, expansion of the polymer layer causes the expandable member 466 to push against the cornea 20. The cornea's resistance to deformation due to the applied force of the expandable member 466 may be sensed by the deformation sensor 468, which provides an indication of intraocular pressure. A feedback circuit may also be provided to determine the amount of current required to obtain a measured level of expansion of the polymer layer.

As described above with respect to FIGS. 3A-3B, the eye-mountable device 410 may be designed to take a single IOP measurement, or multiple IOP measurements over time. In the case of expandable member 466, when the controller 250 ceases to provide an electric current to the expandable member 466, the layer of electroactive polymer will return to its original un-expanded configuration as shown in FIG. 4A. Accordingly, the controller 250 may be configured to apply an electric current to and thereby cause expansion of the expandable member multiple times allowing the IOP sensor 462 to take multiple IOP measurements. The lifetime of the eye-mountable device 410 may depend on the lifetime of the electroactive polymer layer and also on general standards for eye hygiene and contact lens wear.

Figure 5A:
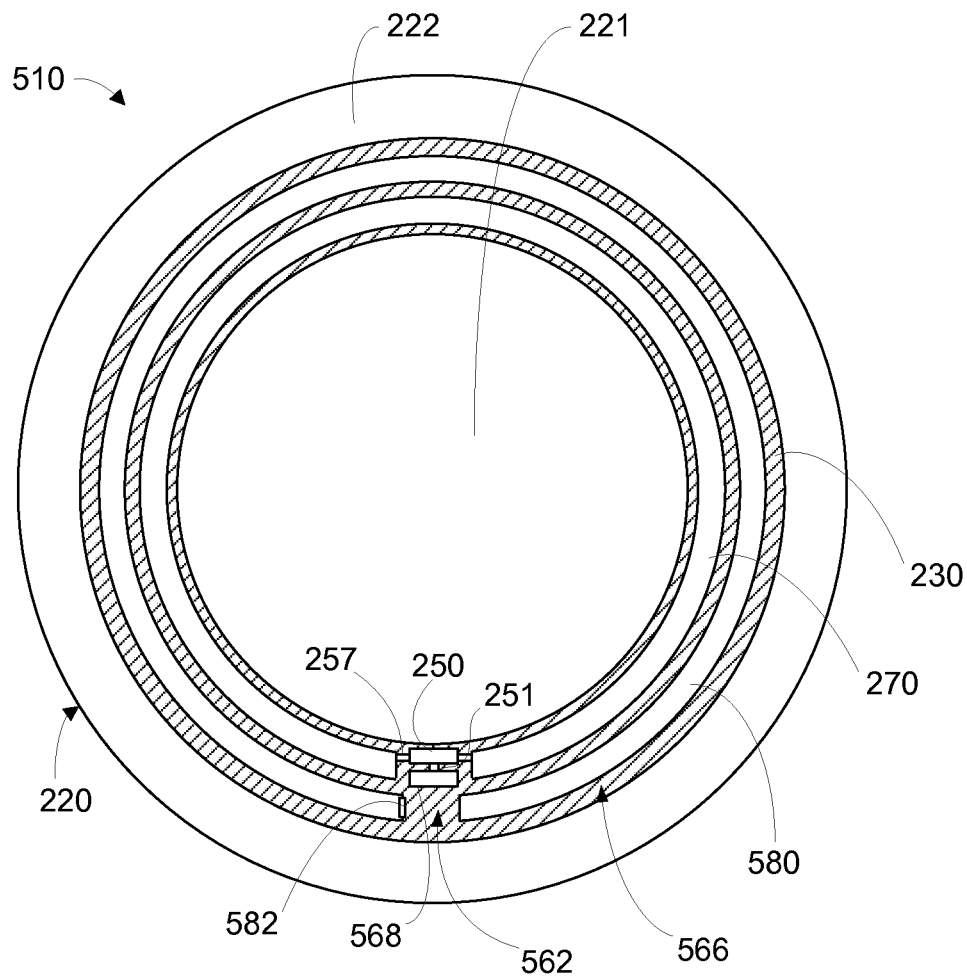
FIG. 5A is a bottom view of an example eye-mountable device including an expandable member, in accordance with an example embodiment.
Figure 5B:
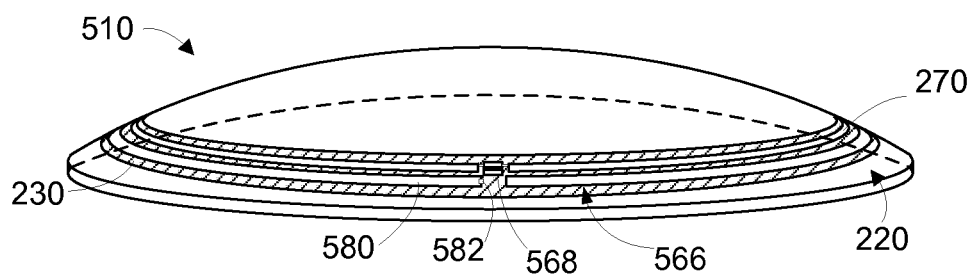
FIG. 5B is a side view of the example eye-mountable device shown in FIG. 5A including an expandable member, in accordance with an example embodiment.

In a third example, as shown in FIGS. 5A-5B, the eye mountable device 510 may include an IOP sensor 562, having an expandable member 566 configured to expand by the degas-driven flow of liquid into one or more reservoirs 580 and a deformation sensor 568 configured to sense the cornea's resistance to deformation by the expandable member 566. The eye mountable device 510 may also include controller 250 electrically connected to a loop antenna 270 via interconnect 257. Deformation sensor 568 may be electrically connected to controller 250 via interconnect 251. All of these components may be disposed on a substrate 230 which may be embedded in a polymeric material 220. All or part of the polymeric material 220 may comprise a porous polymer, such as a silicon-based organic polymer, polydimethylsiloxane (PDMS), polyurethane, polyvinylchloride (PVC), polystyrene, polysulfone, polycarbonate, or polyolefins. The polymeric material 220 may also be a thermoplastic material having sufficiently rapid air permeability and significant free volume.

The one or more reservoirs 580 making up the expandable member 566 may be formed in the polymeric material 220. The reservoirs 580 may be formed at or adjacent to the substrate material 230. Reservoir(s) 580 may be formed in various numbers, shapes, sizes, arrangements and orientations. The reservoir 580 may be of any shape such as, for example, cylindrical, circular, spherical, square, rectangular, and triangular and may be of any desired diameter, any desired depth, and hold any desired volume. Further, the expandable member 566 of the eye-mountable device 510 may include a single reservoir 580, or an array of multiple reservoirs. For example, FIGS. 5A-5B illustrate a single circumferential ring-shaped reservoir 580. Dimensions of the reservoir(s) 580 may range, for example, from about 10 μm to about 3 cm in diameter, from about 10 μm to about 1 cm in depth, and hold a volume of from about 1 pL to about 25 μL or more. In some examples, the reservoir(s) 580 is configured to collect between about 10 and 50 μL of a body fluid. Generally, the reservoir 580 may be formed in the polymeric material 220 of the eye-mountable device 510, such that it can be readily exposed to tear fluid, when placed on the eye. The reservoir 580 may be closed off from the external environment except for an opening 582 provided on a side, end or edge of the eye-mountable device 510. In some examples, a channel (not shown) may connect the opening 582 to the reservoir 580.

Expandable member 566 is configured to expand by drawing tear fluid into reservoir 580 via the mechanism of degas-driven flow. Degas-driven flow does not require external power, but rather takes advantage of the high porosity and air solubility of porous materials by removing air molecules from the porous polymeric material 222 prior to placing the eye-mountable device 510 in contact with the eye and tear fluid. Removing air from the porous polymeric material 222 creates a pressure difference relative to atmospheric pressure. Upon return to atmospheric pressure, the pressure difference causes air inside the reservoir 580 to diffuse into the porous material. Because the reservoir 580 is sealed (i.e., fluid cannot flow in through opening 582 and out through another orifice), a dead-end system is formed. When the eye-mountable device 510 comes into contact with tear fluid, absorption of air into the degassed material from the reservoir 580 draws the body fluid from the opening 582 into the reservoir 580.

To achieve the above-described degas-driven flow, after fabrication, the eye-mountable device 510 is vacuum degassed to remove air and water vapor from the porous polymeric material 222, for example, by placing the device in a vacuum well. Air and water vapor contained in the porous polymeric material 222 is removed by maintaining the eye-mountable device 510 at a low pressure (e.g., less than about 0.3 atm). After vacuum degassing, the eye-mountable device 510 may be immediately used to take IOP measurements or may be stored for later use. Use of vacuum-sealed packaging, such as a Mylar bag, may allow for an eye-mountable device 510 for IOP monitoring to be supplied in a ready-to-use form.

After removing the eye-mountable device 510 from the low-pressure environment following degassing or removal from a vacuum-sealed packaging, the porous polymeric material 220 will reabsorb gas until it reaches equilibrium with the atmosphere. Upon reaching equilibrium with the atmosphere, the expandable member 566 will no longer exhibit degas-driven flow. Therefore, to fill the reservoir 580 using degas-driven flow, the eye-mountable device 510 is brought into contact with the eye and tear fluid at any time point before the degassed device reaches equilibrium with the atmosphere. Various parameters may affect the dynamics of degas-driven flow. For example, geometry of the eye-mountable device 510 and/or expandable member 566, reservoir 580 geometries, type and thickness of the porous polymeric material 220, exposure area, vacuum degassing time, and time at atmospheric pressure prior to contact with tear fluid may affect degas-driven flow.

In operation, the inflow of tear fluid into the reservoir 580 causes expansion of the expandable member 566, which pushes against the cornea (similar to that shown in FIGS. 3B and 4B). The cornea's resistance to that expansion may be detected by deformation sensor 568 and equated to an indication of the IOP of the wearer of the device.

In the above-referenced embodiments, polymeric material 220 may comprise a single, continuous layer of material or may be formed multiple layers of material. In some cases, it may be desirable to form the polymeric material 220 as a composite or laminate material, in which different layers of material have a different stiffness. For example, if the stiffness of the polymeric material 220 is smaller than the stiffness of the cornea 20, expansion of the expandable member 366, 466, 566 may push the eye-mountable device 310, 410, 510 away from the eye, rather than apply a force to the eye. In such cases, the device 310, 410, 510 may not measure intraocular pressure. In one embodiment, polymeric material 220 may be formed as a laminate or composite including an outermost layer (defining convex surface 224) has a higher stiffness than that of the cornea 20. A layer of material adjacent to the cornea 20 (defining concave surface 226) may be less stiff than the outermost layer and may have a stiffness on the same scale as that of the eye. In such a configuration, the eye-mountable device 310, 410, 510 may maintain contact with the cornea 20 during expansion of the expandable member 366, 466, 566.

In the above examples described with reference to FIGS. 3A-3B, 4A-4B, and 5A-5B the cornea's resistance to deformation by the expandable member 366, 466, 566 is indicative of the intraocular pressure of the wearer of the device. Generally, the higher the IOP, the more resistant the cornea will be to deformation, and the harder it will be for the expandable member 566 to expand against the cornea. This resistance to deformation can be measured by a deformation sensor 368, 468, 568 using a range of different techniques. Deformation sensor 368, 468, 568 may include one or more mechanical, optical, acoustical, pneumatic, and electrical sensors. In some examples, the deformation sensor 368, 468, 568 may measure the deflection or displacement of the corneal surface 22 in response to a force applied by the expandable member 366, 466, 566. Additionally or alternatively, deformation of the expandable member 366, 466, 566 against the cornea 20 may be detected. In further examples, IOP may be determined based on the amount of expansion (i.e. volume and rate of expansion) of the expandable member. While the position and orientation of deformation sensor 368, 468, 568 is shown schematically in FIGS. 3A-3B, 4A-4B and 5A-5B as being alongside or adjacent to the controller or expandable member, other configurations are contemplated.

For example, with respect to the embodiment discussed with respect to FIGS. 5A-5B, the amount of tear fluid pumped into the reservoir 580 by degas-driven flow will depend on the reservoir's ability to expand against the cornea, which will depend on the deformability of the cornea and, therefore, the IOP. While deformation sensor 568 is shown schematically in FIGS. 5A-5B as being positioned adjacent to the controller 250, the deformation sensor 568 may be provided as one or more electrodes (not shown) positioned on the inner and outer-facing surfaces of the reservoir 580 and electrically connected to controller 250. Expansion of the reservoir 580 will change the distance between the electrodes, thereby changing the conductance of the sensor. In another example, deformation sensor 568 may include a strain gauge (not shown) positioned on an expanding surface of the expandable member 566 and electrically connected to the controller 250. As the expandable member 566 expands, the strain gauge will stretch, thereby changing the resistance of the gauge. The change in resistance may be equated to the expanded volume of the expandable member 566, which may be equated to the IOP of the wearer of the device.

Analysis of the data collected by the IOP sensor 362, 462, 562 may be conducted directly on the eye-mountable device 310, 410, 510, or in a separate computing device, such as an external reader 180. As described above, data collected by the IOP sensor may be transmitted to the reader and processed to determine an indication of the IOP of the wearer of the device. In other examples, the eye-mountable device may be provided with a processor and memory, which may have program instructions stored thereon, for determining an indication of the wearer's IOP directly on the device.

Figure 6A:
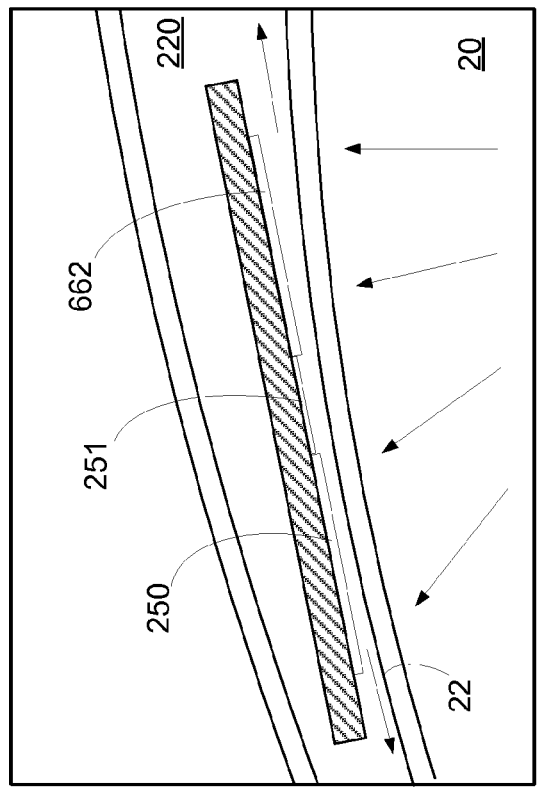
FIGS. 6A-6B are side cross-section views enhanced to show the example eye-mountable device when mounted against the cornea of an eye and operation of an intraocular pressure sensor, in accordance with an example embodiment.
Figure 6B:
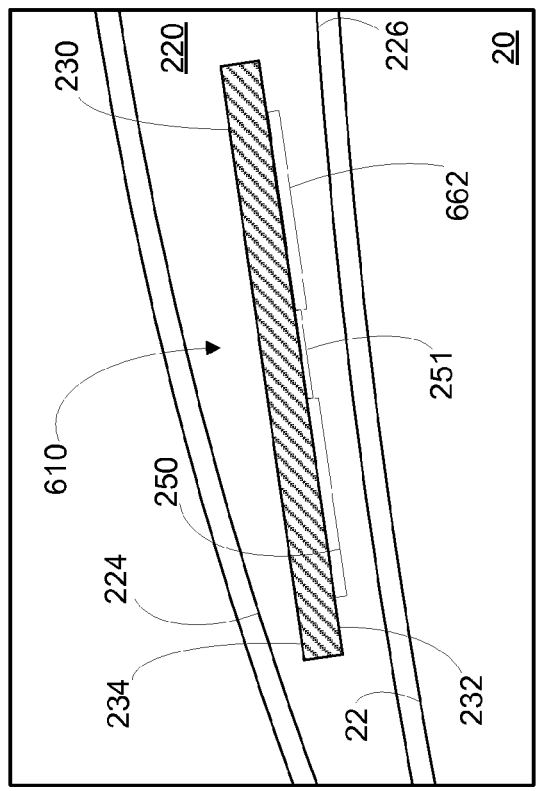

In a further aspect, the eye mountable device may be configured to passively detect the wearer's IOP without the use of an expandable member to apply a force to the cornea. For example, as schematically shown in FIGS. 6A-6B, the IOP sensor 662 of eye mountable device 610 may be provided as a typical strain element or an array of strain elements disposed on or adjacent to the substrate 230 or embedded in the polymeric material 220. The IOP sensor 662 may detect IOP through some direct deformation or deflection of the sensor due to a change in curvature and/or circumference of the surface of the eye. For example, the sensor may consist of a resistive, capacitive, or inductive strain element or an array of co-planar resistive strain elements, such as ring electrodes. The strain element(s) of the IOP sensor 662 may be made, at least partly, of a resistive or piezoresistive material, the resistance of which varies based on the gauge strain or deformation. As shown in FIG. 6B, a change in IOP may cause a change in the circumference of the eye. In turn, the circumference of the eye mountable device 610 situated on the cornea 20 will also change, resulting in a change in configuration (e.g., length, thickness) of the strain element(s) of the IOP sensor. The resulting deformation of the strain element(s) on the contact lens changes the resistance, capacitance or inductance of the material, thereby changing the current flowing through the element(s), which can be detected by the controller 250. The measured change in resistance, inductance or capacitance of the strain gauge may be equated to the change in IOP of the wearer of the device.

Figure 7B:
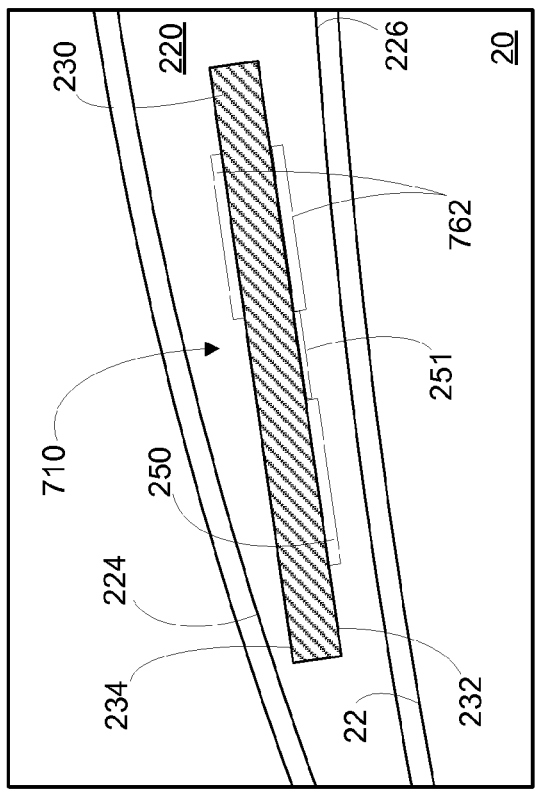
FIGS. 7A-7B are side cross-section views enhanced to show the example eye-mountable device when mounted against the cornea of an eye and operation of an intraocular pressure sensor, in accordance with an example embodiment.
Figure 7A:
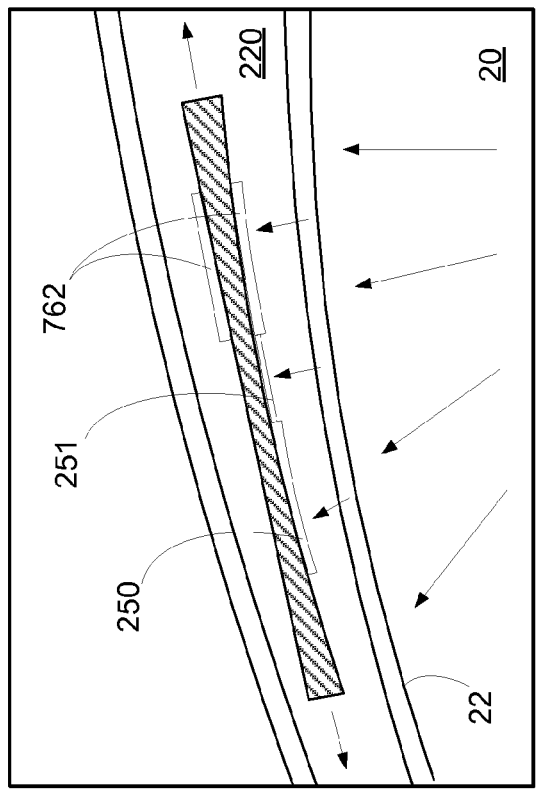

Alternatively, the eye mountable device 710 may also include an IOP sensor 762 comprising one or more strain elements lying in parallel planes within the contact lens, as shown in FIGS. 7A-7B. The electrodes of the strain elements may or may not be electrically connected, depending on whether the IOP sensor 762 is configured as a capacitive or conductive element. As shown in FIG. 7B, a change in IOP will change the curvature of the surface of the cornea 22 and, as a result, the curvature of the eye mountable device 710 and the distance between the electrodes of the sensor 762. The change in distance between the electrodes will change the electric field between them, thereby changing the conductance or capacitance of the sensor. The change in conductance or capacitance across the sensor as measured by the controller 250 may be equated to the change in IOP. In another aspect, the IOP sensor may be provided as a set of or an array of co-planar interdigitated electrodes. Deflection of the eye-mountable device by a change in IOP will change the distance between the fingers of the electrodes, causing a measurable change in conductance or capacitance of the sensor from which IOP may be determined.

VII. Example Methods

Figure 8:
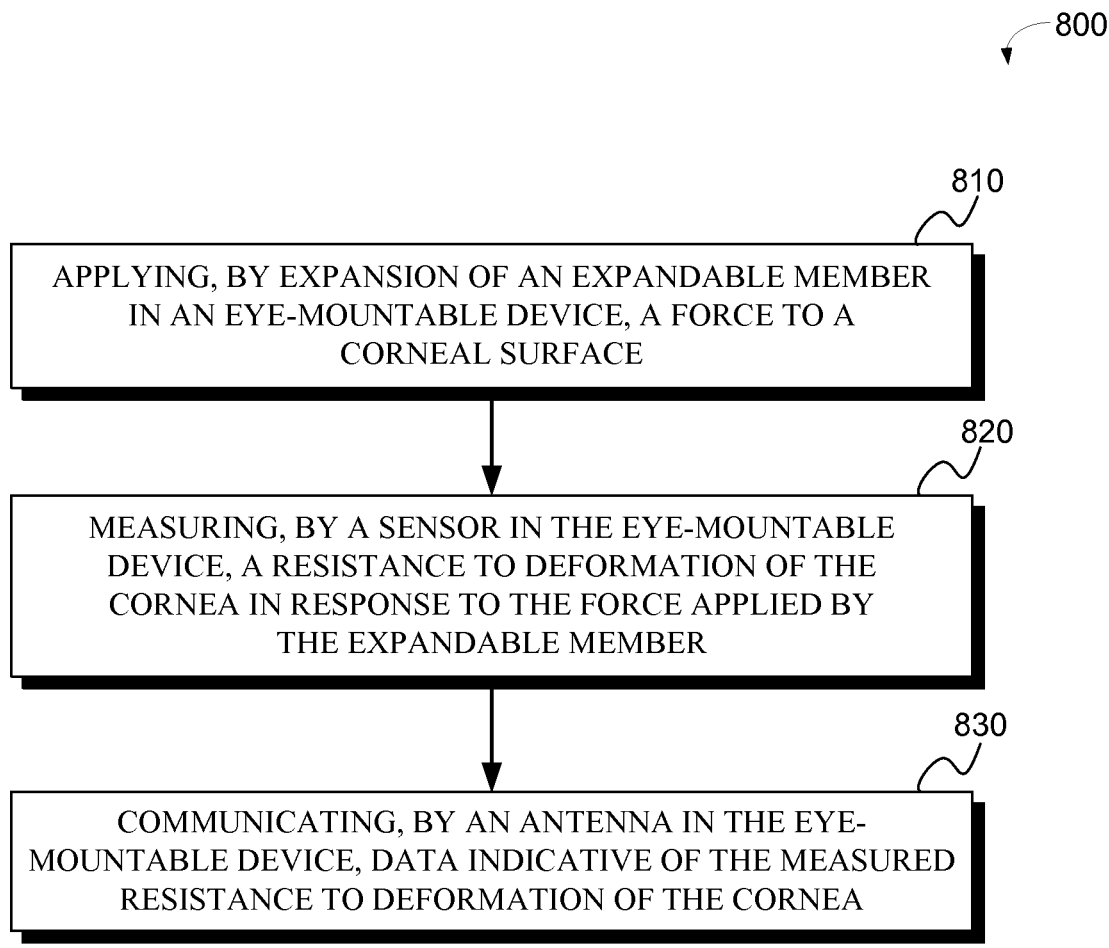
FIG. 8 is a flow chart of an example method, in accordance with an example embodiment.

FIG. 8 is a flow chart of an example method 800. Method 800 can be carried out by an eye-mountable device configured to detect an indication of intraocular pressure of an eye of a wearer of the device. The device may include an expandable member and a sensor. In a first step, a force is applied to the corneal surface of an eye by expansion of an expandable member in an eye-mountable device expands (810). The eye-mountable device may be provided as any eye-mountable device having an expandable member configured to apply a force to the corneal surface, including any one of the eye-mountable devices 310, 410, and 510 as discussed above. The expandable member may include at least one vacuum de-gassed reservoir disposed at least partially within the transparent polymeric material of the eye-mountable device, which may include a silicon-based porous organic polymer. The at least one expandable member may be configured to expand by drawing a volume of tear fluid through an opening and into the reservoir upon equilibrating to atmospheric pressure with the concave surface mounted over the corneal surface. In another example, the expandable member may be a layer of electroactive polymer, such as polypyrrole, polythiophene, polyaniline, or polyacetylene, configured to expand in a direction substantially perpendicular to the corneal surface in the presence of an electric field. In yet another aspect, the expandable member may be provided as a chamber disposed at least partially within the transparent polymeric material containing a solid material, such as sodium azide, potassium azide, and lithium azide, configured to undergo a phase change from a solid to a gaseous state upon exposure to an electrical signal.

In a second step, a sensor in the eye-mountable device measures a resistance to deformation of the cornea in response to the force applied by the expandable member. The cornea's resistance to deformation by the expandable member is related to the intraocular pressure. As described above, the cornea's resistance to deformation may be detected in a number of ways and by various sensors. For example, the resistance data may be one or more of: (1) a measured displacement, deformation or deflection of the expandable member against the corneal surface in response to applying said force to the corneal surface; (2) a measured displacement, deformation or deflection of the corneal surface in response to applying said force to the corneal surface; or (3) a measured change in volume of the expandable member or rate of change in volume of the expandable member. The sensor may include one or more of a mechanical, optical, acoustical, pneumatic, or electrical measurement device.

In a third step, the eye mountable device communicates the data indicative of the measured resistance to deformation of the cornea by an antenna. In some examples, the communicated data is received by an external reader. The external reader may determine an intraocular pressure of the eye based on the measured resistance to deformation of the cornea. An indication of the intraocular pressure may be displayed on the external reader.

VII. CONCLUSION

The present disclosure is not to be limited in terms of the particular embodiments described in this application, which are intended as illustrations of various aspects. Other embodiments can be utilized, and other changes can be made, without departing from the spirit or scope of the subject matter presented herein, as will be apparent to those skilled in the art. It will be readily understood that the aspects of the present disclosure, as generally described herein, and illustrated in the figures, can be arranged, substituted, combined, separated, and designed in a wide variety of different configurations, all of which are explicitly contemplated herein. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of example systems, devices, and methods with reference to the accompanying figures. In the figures, similar symbols typically identify similar components, unless context dictates otherwise. The example embodiments described herein and in the figures are not meant to be limiting. It should be understood that other embodiments can include more or less of each element shown in a given figure. Further, some of the illustrated elements can be combined or omitted. Yet further, an example embodiment can include elements that are not illustrated in the figures.

It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Further, some embodiments of the system and/or body-mountable devices may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

What is claimed is:

1. An eye-mountable device comprising:
   a transparent polymeric material having a concave surface and a convex surface, wherein the concave surface is configured to be removably mounted over a corneal surface of an eye and the convex surface is configured to be compatible with eyelid motion when the concave surface is so mounted;
   an antenna at least partially embedded in the transparent polymeric material;
   an expandable member at least partially embedded in the transparent polymeric material and configured to expand and apply a force to the corneal surface;
   a sensor at least partially embedded in the transparent polymeric material configured to detect a resistance to deformation of the cornea in response to the force applied by the expandable member; and
   control electronics at least partially embedded in the transparent polymeric material, wherein the control electronics are configured to: (i) use the sensor to measure the resistance to deformation of the cornea; and (ii) use the antenna to communicate data indicative of the measured resistance to deformation of the cornea to an external reader, wherein the resistance to deformation of the cornea in response to the force applied by the expandable member is indicative of intraocular pressure of the eye.

2. The device of claim 1, wherein the expandable member comprises at least one vacuum de-gassed reservoir disposed at least partially within the transparent polymeric material and having an opening, wherein the at least one expandable member is configured to expand by drawing a volume of tear fluid through the opening and into the reservoir upon equilibrating to atmospheric pressure with the concave surface mounted over the corneal surface.

3. The device of claim 2, wherein the transparent polymeric material comprises a silicon-based porous organic polymer.

4. The device of claim 1, wherein the expandable member comprises a layer of electroactive polymer configured to expand in a direction substantially perpendicular to the corneal surface in the presence of an electric field.

5. The device of claim 4, wherein the electroactive polymer is chosen from the group consisting of polypyrrole, polythiophene, polyaniline, and polyacetylene.

6. The device of claim 1, wherein the expandable member comprises a chamber disposed at least partially within the transparent polymeric material and containing a solid material configured to undergo a phase change from a solid to a gaseous state upon exposure to an electrical signal.

7. The device of claim 6, wherein the solid material is chosen from the group consisting of sodium azide, potassium azide, and lithium azide.

8. The device of claim 1, wherein the data comprises one or more of measured displacement, deformation or deflection of the expandable member against the corneal surface in response to applying said force to the corneal surface.

9. The device of claim 1, wherein the data comprises one or more of measured displacement, deformation or deflection of the corneal surface in response to applying said force to the corneal surface.

10. The device of claim 1, wherein the data comprises one or more of a measured change in volume of the expandable member or rate of change in volume of the expandable member.

11. The device of claim 1, wherein the sensor comprises one or more of a mechanical, optical, acoustical, pneumatic, or electrical measurement device.

12. The device of claim 11, wherein the sensor comprises a strain gauge.

13. The device of claim 12, wherein the strain gauge comprises one or more resistive elements.

14. The device of claim 12, wherein the strain gauge comprises one or more interdigitated electrodes.

15. The device of claim 12, wherein the strain gauge comprises one or more electrodes configured to measure a change in capacitance.

16. The device of claim 12, wherein the strain gauge comprises one or more electrodes configured to measure a change in conductance.

* * * * *